United States Patent [19]
Watkins

[11] Patent Number: 5,100,779
[45] Date of Patent: Mar. 31, 1992

[54] METHOD FOR DETERMINING FUNCTION OF A UNIQUE CYTOCHROME P-450 ACTIVITY

[76] Inventor: Paul B. Watkins, 40 Barton North, Ann Arbor, Mich. 48105

[21] Appl. No.: 520,115

[22] Filed: May 4, 1990

Related U.S. Application Data

[63] Continuation-in-part of Ser. No. 253,196, Oct. 4, 1988, abandoned.

[51] Int. Cl.$^5$ .................. C12Q 1/26; A61K 49/00; G01N 31/00; G01N 33/48
[52] U.S. Cl. .................. 435/25; 435/4; 435/25; 424/9; 436/133; 436/56; 436/57; 436/500
[58] Field of Search .................. 424/9; 435/19, 4, 25; 436/133, 171, 56, 57, 900; 250/343; 356/51

[56] References Cited

PUBLICATIONS

Bircher et al (1981) Exhalation of Isotopic CO$_2$, Methods in Enzymology 77:3-9.
The Merick Index 1983, Entries 2748 and 3524.
Bruch et al. (1987) The 14CO$_2$ Breath Test, Arch. Toxicol. 60:81-5.
Kronbach et al (1988), Cyclosporcie Metabolism in the Human Liver, Clin. Pharm. Ther. 43:630-5.
Brueck et al, Chemical Abstracts, 53776s, vol. 107, 1987.
Coates et al, Chem. Abst, 139172h, vol. 96, 1982.
Wasowicz et al, Chem. Abst. 177490q, vol. 101, 1984.
Wathair et al, Chem. Abst., 1502057z, vol. 110, 1989 (Fourth Record).

*Primary Examiner*—Robert A. Wax
*Assistant Examiner*—David R. Preston
*Attorney, Agent, or Firm*—Reising, Ethington, Barnard, Perry & Milton

[57] ABSTRACT

A method for determining the function of a unique cytochrome activity of the type which uniquely catalyses the N-demethylation of erythromycin in a patient's body, the method including the steps of ingesting a known quantity of a N-methyl carbon labeled erythromycin solution, the N-methyl carbon demethylated from the erythromycin being metabolized to an exhaled carbon labeled metabolite. A sample of exhaled breath containing a known amount of exhaled carbon metabolite is collected at a known interval of time after ingestion of the erythomycin solution. The quantity of labeled carbon metabolite is detected in the exhaled sample to determine the rate of labeled carbon elimination after the known time interval as an indication of the unique cytochrome function.

7 Claims, 6 Drawing Sheets

CYCLOSPORINE BLOOD LEVELS

Fig-7A — 3mg/kg/day

Fig-7B — 5mg/kg/day

Fig-7C — 7.5mg/kg/day

METHOD FOR DETERMINING FUNCTION OF A UNIQUE CYTOCHROME P-450 ACTIVITY

This is a continuation-in-part of copending application Ser. No. 07/253,196, filed on Oct. 4, 1988, abandoned.

TECHNICAL FIELD

The present invention relates to a method for determining the function of an enzyme present in the liver and in the intestinal mucosa. More specifically, the invention relates to a method for determining the function of a unique enzyme activity of the type which uniquely catalyses the N-demethylation of erythromycin in a patient's body.

BACKGROUND ART

The cytochromes P-450 are membrane bound hemoproteins abundant in the liver. These proteins play a critical role in the metabolism of many endogenous and exogenous compounds including steroid hormones and drugs. Reactions catalyzed by cytochromes P-450 often produce metabolites less bioactive and more readily eliminated than are the parent compounds. To date, there have been at least 21 cytochromes P-450 purified from rat liver, each with characteristic structure, substrate binding affinities, and in some cases, differential regulatory responses to drugs or other xenobiotics. Black and Coon (1986) Comparative Structures of P-450 Cytochromes. In Cytochromes P-450: Structure, Metabolism and Biochemistry. P. R. Ortiz Dey Montellano editor. Plenman Publishing Corp., New York. Because each cytochrome appears to reflect expression of a unique gene, a standard nomenclature has been proposed based on dividing the P-450 genes into families and subfamilies according to nucleotide sequence homology.

Research has shown significant interpatient differences in the liver concentrations and activities of some cytochromes P-450. For example, the deficiency in the ability to metabolize debrisoquine, an antihypertensive medication, has been shown to be inherited as an autosomal recessive trait and appears to result from one of several mutations in the gene coding for a single liver cytochrome P-450 (P-450 IID gene family). Mahgoub, A et al 1977. Polymorphic hydroxlation of debrisoquine. Lancet 2:584–586. This defective cytochrome has been related to adverse reactions to many medications as well as other medical risks.

Predictions of adverse reactions to medications will require safe and noninvasive means to phenotype individuals in vivo for each of the cytochromes P-450 that demonstrate interpatient differences in catalytic activity and which play important roles in metabolism of drugs. One approach illustrated by Hepner and Vesell, N-Engl J Med 291:1384–1388, is by the aminopyrine breath test in which carbon labeled N-dimethyl aminopyrine is administered to patients and, because the radio-labeled carbon atom in the cleaved methyl group is largely converted to bicarbonate in vivo, the rate of demethylation can be conveniently monitored as the rate of production of radio-labeled carbon dioxide in the breath. Unfortunately, aminopyrine is demethylated twice by at least two different forms of cytochrome P-450 which have not yet been identified.

It has recently been discovered that the elimination of cyclosporine A (CsA) from the human body depends on its metabolism in the liver by cytochrome P-450III. Kronbach T. et al, Cyclosporine metabolism in human liver: Identification of a cytochrome P-450III gene family as the major cyclosporine-metabolizing enzyme explains interactions of cyclosporine with other drugs. Clin Pharmacol Ther 1988; 43:630–5. Combalbert J. et al Metabolism of Cyclosporin A. IV. Purification and identification of the rifampicin-inducible human liver cytochrome P-450 (Cyclosporin A Oxidase) as a product of P450IIIA gene subfamily. Drug Metabolism and Disposition 1989; 17:197–207. P-450IIIA is a Phase 1 enzyme whose catalytic activity varies many fold among patients. Guengerich F. P. et al, Characterization of rat and human liver microsomal cytochrome P-450 forms involved in nifedipine oxidation, prototype for genetic polymorphism in oxidative drug metabolism. J Biol Chem 1986; 261:5051–60; Wrighton S. A. et al, Purification of a human liver cytochrome P-450 immunochemically related to several cytochromes P-450 purified from untreated rats, J Clin Invest 1987; 80:1017–22.

CsA is an immunosupressive drug widely used to prevent allograft rejection in transplant recipients and appears to be useful in the treatment of many common autoimmune diseases. Bach J-F. Cyclosporine in autoimmune diseases. Transplantation Proceedings 1989; XXI (Suppl 1):97–113. In an attempt to limit toxicity while maximizing the therapeutic effects of CsA, blood levels are usually closely monitored for at least several weeks after patients begin treatment with CsA, and the daily dose is adjusted to achieve a trough blood level within a relatively narrow range. Kennedy MS, et al, Correlation of serum cyclosporine concentration with renal dysfunction in marrow transplant recipients. Transplantation 1985; 40:249–53. Irschik E. et al, Cyclosporine blood levels do correlate with clinical complications. Lancet 1984; 2:692–3. Konigsrainer A. et al, Rigid-dose regimen versus blood level-adjusted cyclosporine in elderly cadaveric renal allograft recipients. Transplantation 1988; 46:631–44. Moyer T. P. et al, Cyclosporine nephorotoxity is minimized by adjusting dosage on the basis of drug concentration in blood. Mayo Clin Proc 1988; 63:241–7. This procedure is often a tedious and costly process because the daily dose of CsA required to achieve a target blood level can vary at least 10 fold among patients. Kahan B. D et al, Optimization of cyclosporine therapy in renal transplantation by a pharmacokinetic strategy. Transplantation 1988; 46:631–44. Thus, an empirical initial dose of CsA will produce either potentially sub-therapeutic or potentially toxic blood levels in many patients. Furthermore, because CsA has a relatively long blood half-life (Ptachcinski, R. J. et al, Clinical pharmacokinetics of cyclosporine. Clinical Pharmacokinetics 1986; 11:107–32), it can take many days or weeks to arrive at an appropriate CsA dosing regiment for some patients. At some medical centers, CsA pharmacokinetics are routinely determined to better estimate individual dosing requirements. These studies can take several days to perform and have not become a standard practice.

The U.S. Pat. No. 4,676,974 to Hofmann et al, issued June 30, 1987 discloses a breath test method for pancreatic exocrine function wherein a radioactive labeled ester such as cholesterol octanoate is ingested in the body and is hydrolyzed by pancreatic enzymes and oxidized to labeled carbon dioxide which is expired in the breath. The rate of the appearance of the labeled carbon dioxide in the breath is a function of the rate of hydrolysis of pancreatic enzymes which in turn reflects pancreatic exocrine function.

The U.S. Pat. No. 4,298,347 to Walsh, issued Nov. 3, 1981, discloses a method for the analysis of exhaled carbon dioxide for clinical diagnostic application which contains a mixture of $^{13}CO_2$ and $^{12}CO_2$. The method relates strictly to a carbon dioxide breath test but does not relate at all to the analysis of an enzyme function.

The U.S. Pat. Nos. 3,792,272 to Harte et al, issued Feb. 12, 1974 and 4,407,152 to Guth, issued Oct. 4, 1983 relate to breath test devices for detecting the concentration of ethyl alcohol in the breath.

Brueck et al, CHemical Abstracts 107, 53776s (1987) discloses a carbon-14 dioxide ($^{14}CO_2$) breath test. The article only refers to the measurement of "modified" or "altered" P-450 activity. That is, the article addresses only changes in breath tests brought about by induction or inhibition of drug metabolizing enzymes, including P-450's, by the administration of other drugs. The article does not address the concept of quantitating the activity of a P-450 which uniquely catalyzes N-demethylation in "normal" individuals. The article does not discuss the idea that breath tests can specifically measure specific forms of P-450. The article merely speculates that the reason that phenobarbital treatment did not increase the production of $CO_2$ from methoxyacetanilid was due to alterations in the one carbon pool kinetics. However, another reason for this effect is that the form to P-450 that metabolizes methoxyacetanilid is not inducible by phenobarbital. Further, the article studies exclusively O-demethylation reactions and not N-demethylation. The only reference to humans in the article is a speculation that it may be possible to develop a diagnostic analysis for the metabolic disorders by means of a breath test technique but the article does not foresee or suggest that a breath test may be suitable for determining the activity of specific P-450's in healthy individuals.

Coates et al, Chemical Abstracts 96, 139–172h (1982) discusses the detection of deconjugation of bile salts with a carbon-14 labeled carbon dioxide breath test. The abstract does not relate at all or even suggest a test based on N-demethylation nor does it relate to or suggest a breath test that may be suitable for determining the activity of specific P-450's in healthy individuals.

The present invention relates to a novel approach for characterizing the major glucocorticoid-inducible cytochromes P-450 (P-450 IIIA a gene family) present in the livers and intestine of rats and man. Since P450IIIA enzymes catalyze and in most instances, limit the rate of erythromycin N-demethylation in liver microsomes prepared from their respective, the rate of production of labeled carbon dioxide in breath after injection of a test dose of radio-labeled N-methyl erythromycin provides a convenient and selective measure of the catalytic activity of these cytochromes in vivo.

Because P-450IIIA catalyses the N-demethylation of erythromycin, applicant reasoned that a patient's ability to demethylate erythromycin may be useful in predicting an appropriate dosing regiment for CsA.

SUMMARY OF THE INVENTION

In accordance with the present invention, there is provided a method for determining the function of unique cytochrome P-450 activity of the type which uniquely catalyses the N-demethylation of erythromycin in a patient's body, the method including the steps of ingesting a known quantity of N-methyl carbon labeled erythromycin solution, the N-methyl carbon demethylated from the erythromycin being metabolized to an exhaled carbon labeled metabolite. A sample of exhaled breath containing a known amount of exhaled carbon metabolite is collected at a known interval of time after ingestion of the erythromycin solution. The quantity of labeled carbon metabolite in the exhaled sample is detected to determine the rate of carbon elimination after the known time interval as an indication of the unique cytochrome P-450 function.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

The present invention provides a novel method for determining the function of a unique cytochrome P-450 activity of the type which uniquely catalyses the N-demethylation of erythromycin in a patient's body. The unique cytochrome P-450 has been characterized as the major P-450 III A gene family present in the livers and intestinal mucosa of rats and man. It has been shown that the catalytic activity of P-450IIIA varies 3-6 fold between patients.

This variation of three to six fold difference is very important in how patients respond to certain drugs. The present invention enables a physician to accurately type patients in this regard. That is, the ability of the patient to metabolize a drug is directly proportional to the amount of active drug in the patient's system. The three to six fold difference between patients in catalytic activity of p-450IIIA can result in some patients receiving a specific set recommended dose of drug and having an effective blood level, a certain group of patients receiving the same dose of drug and having ineffective blood levels and other patients receiving the same dose of drug and receiving a toxic blood level. An example of this phenomena occurs with patients receiving CsA. The target blood level of CsA can be achieved by a daily dose of CsA; in patients that level can vary at least 10 fold. Kahan B. D. et al, Optimization of cyclosporine therapy in renal transplantation by a pharmacokinetic strategy. Transplantation 1988; 46:631-44. Furthermore, because CsA has a relatively long blood half life, and may take many days or weeks to arrive at an appropriate CsA dosing regiment for some patients. It is expected that the determination of the function of this unique cytochrome activity in an individual can be correlated to the metabolism of various drugs as this cytochrome is responsible for the metabolism of such drugs as ethinylestradiol, nifedipine, quinidine and cyclosporine A. For example, it has been recently shown that the P-450 III A cytochrome present in liver catalyzed the conversion of cyclosporine A to its major metabolites Kronbach et al, 1988 Clin. Pharmacol. Ther. 43:630-5. Therefore, the present invention provides a novel means of predicting the metabolism of drugs such as cyclosporine and eventually the dosing of cyclosporine in patients.

Generally, in accordance with the present invention, a patient ingests, by injection or orally, a known quantity of N-methyl carbon labeled erythromycin. The N-methyl carbon demethylated from the erythromycin is metabolized to an exhaled carbon labeled metabolite. A sample of the exhaled breath containing a known amount of the exhaled carbon metabolite is collected at a known interval of time after ingestion of the erythromycin solution. The quantity of labeled carbon metabolite in the exhaled sample is detected to determine the rate of labeled carbon elimination after the known time interval as an indication of the unique cytochrome P-450 function.

More specifically, a preferred method in accordance with the present invention utilizes the metabolic pathway of the N-methyl carbon labeled erythromycin. The carbon of the N-methyl group of the erythromycin can be labeled as $^{14}C$ or $^{13}C$. $^{14}C$ labeled N-methyl erythromycin is commercially produced by New England Nuclear Corporation.

A preferred patient protocol provides for a patient to be given one to three microcuries of $^{14}C$ N-methyl erythromycin dissolved in 2 ml of dextrose and water by intravenous injection. The patient is asked to blow bubbles through a device containing a one way valve into 4 ml of 0.5M hyamine (as supplied by Sigma Corporation) in ethanol to which a small amount of phenophthaline as been added as a pH indicator. This specific solution will trap exactly 2 mM of carbon dioxide and after this amount is trapped, the pH of the sample will change and the blue color will disappear. The patient is told to blow bubbles into the solution until the color disappears. The collection step is performed ten minutes after the injection of the radio-labeled erythromycin. If radio-labeled carbon is used the specific activity of the $^{14}C$ is then determined by scintillation counting. Devices known in the art are used to determine the ratio of $^{13}C$ to $^{12}C$ if carbon-13 is utilized to label the N-methyl group of erythromycin.

Increased activity over a norm is an indicator of relatively high metabolic activity. Such high activity can be an indication of increased metabolism vis a vis the normal activity of a test group. This knowledge can be correlated to drug dosing, possibly increasing the efficiency of dosing and decreasing the chances of overdosing by identifying poor metabolizing patients. A finding of low enzyme activity can indicate an decrease in dosage.

The rate at which the radio-label was exhaled at the collection time point is then determined as the estimate of endogenous carbon dioxide production (a well known function of height and weight).

EXPERIMENTAL EVIDENCE

Figure 1:
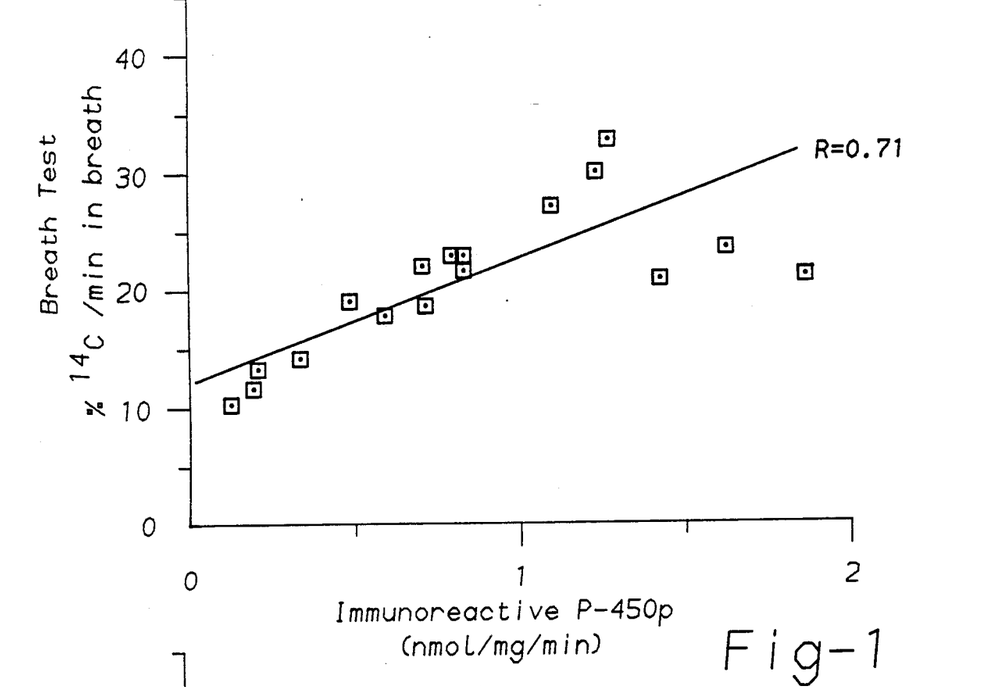
FIG. 1 is a plot correlating expired end radio-labeled carbon dioxide and liver microsomal concentrations of a major P450IIIA enzyme protein, termed p-450p, in rats.
Figure 2:
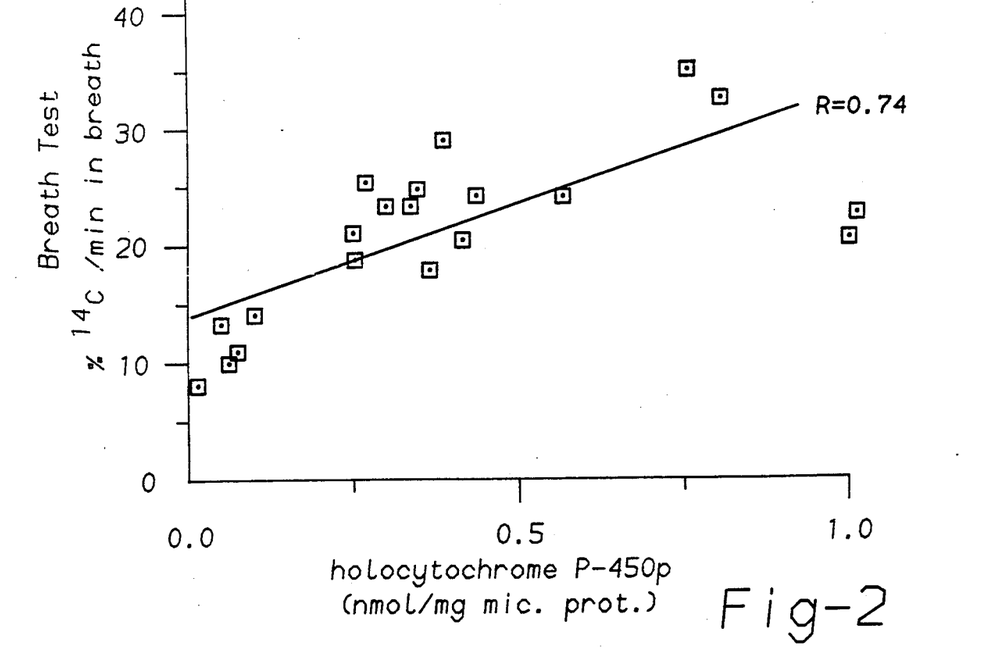
FIG. 2 is a plot correlating expired radio-labeled carbon dioxide and the microsomal concentration of the catalytically active, or holocytochrome P-450P in rats.

In developing a practical method to estimate the amounts of P-450IIIA in patients, radio-labeled $^{14}C$ N-methyl erythromycin was injected into rats that had been pretreated with dexamethasone inducer of a major rat P-450IIIA enzyme termed P-450p, or with inducers of other forms of cytochrome P-450. The rate of demethylation of this substrate, measured simply as the total production radio-labeled carbon dioxide in the breath during 135 minutes, correlated well with the concentrations of immunoreactive P-450p protein ($r=0.70$)(protein alone), holocytochrome P-450p ($r=0.70$)(catalytically active enzyme including heme and protein to correlate as control), or with erythromycin N-demethylase activity ($r=0.90$) determined in liver microsomes prepared from each rat. FIG. 1 shows a correlation between expired radio-labeled carbon dioxide and the microsomal concentration of P-450p protein. FIG. 2 shows the correlation between expired radio-labeled carbon dioxide and the microsomal concentration of holocytochrome P-450p. The breath test results from each rat were compared to the concentrations of immunoreactive P-450p and of holocytochrome P-450p determined in the liver microsomes of the rats. Rats were pretreated with either phenobarbital or dexamethasone, potentiators of P-450 activity.

Figure 3:
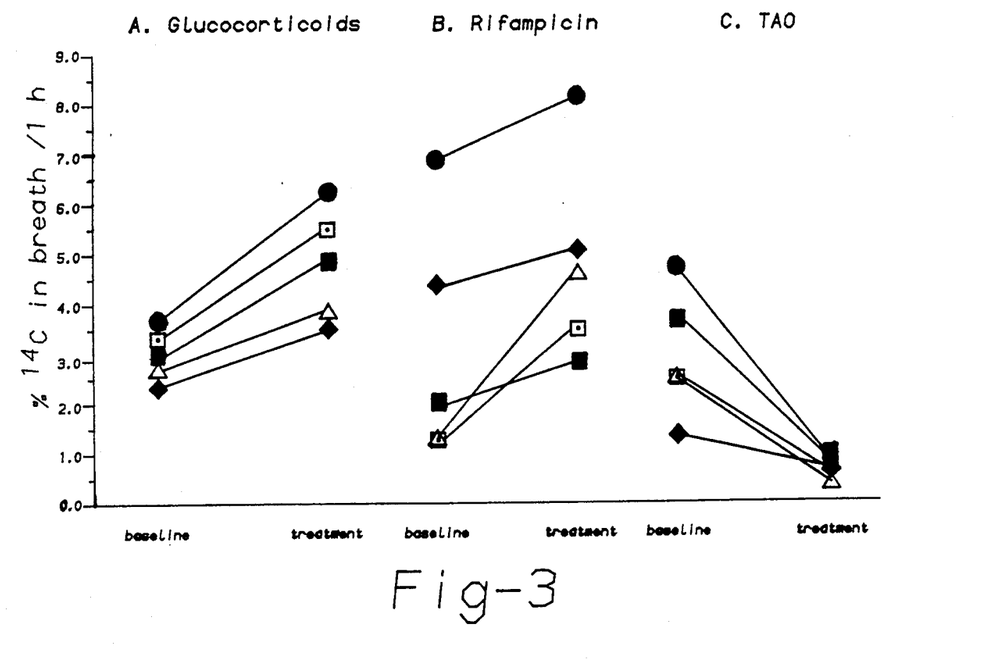
FIG. 3 is a plot illustrating the effect of various medications on patients' breath test results administered in accordance with the present invention wherein patients were treated with glucocorticoids, rifampicin, or triacetyloleandomycin.

In additional experiments shown in FIG. 3, $^{14}C$ N-methyl erythromycin was administered to thirty patients. There was a six fold individual variation in breath radio-labeled carbon dioxide production seemingly unrelated to patient's medication, smoking status or age. It was further found that the average breath test values were two fold greater in females as compared to male patients (p 0.01). It was further found that breath radio-labeled carbon dioxide production rose in patients retested after treatment with the P-450 III A inducer dexamethasone (p 0.05) or rifampicin (p 0.05) and was decreased after treatment with the p-450IIIA inhibitor triacetyloleandomycin (p 0.05).

The above discussed biochemical tests suggest that the erythromycin breath test in accordance with the present invention reflects p-450IIIA activity in man. For all tests given to patients, there was a linear correlation between the total amount of radio-labeled eliminated in one hour and the rate of radio-labeled elimination measured in the single collection at 10 minutes. The range of breath test values was four to six fold among patients not taking medications known to influence the activities of either P-450p in rats or the related cytochromes in other species. However, the results for a given patient were consistent. On repeat testing of ten patients the breath test results were not changed by more than 27%.

In patient tests, treatment with glucocorticoids resulted in significant increases in breath test values, as illustrated in FIG. 3. There was an average increase of 55% (p 0.05).

Figure 4:
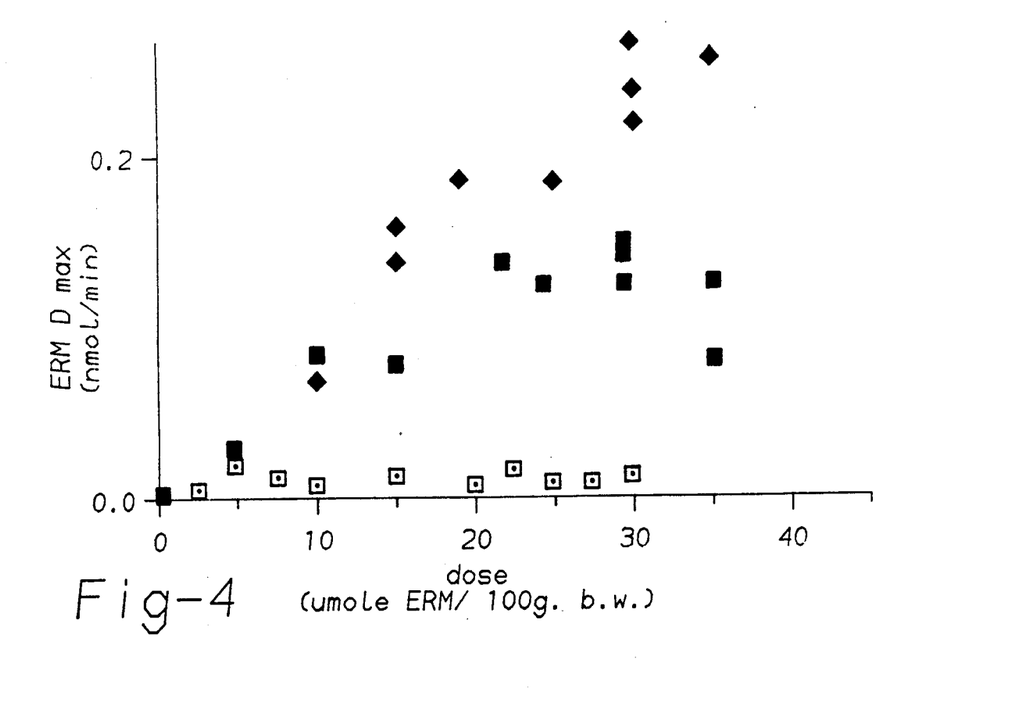
FIG. 4 is a plot showing the maximal rate of in vivo demethylation as a function of dose of erythromycin administered in control and dexamethasone pretreated rats.

There is therefore compelling evidence that the rate of in vivo metabolism of erythromycin, as measured by the breath test in accordance with the present invention, can predict the catalytic activity of P-450p in rats. In rats given radio-labeled N-methyl erythromycin, the ability to convert the radio-labeled carbon to breath carbon dioxide is saturable as shown in FIG. 4. FIG. 4 illustrates the maximal rate of in vivo demethylation as a function of dose of erythromycin administered in control and dexamethasone pretreated rats. Adult female rats were gavaged with high dose dexamethasone (300 mg/kg/day$\times$3, shown as diamonds on the plot) low dose dexamethasone (20 mg/kg/day$\times$2, shown as filled-in squares on the plot) or vehicle alone (2 days, shown as open boxes on the plot). Each rat then received intravenous injections containing identical amounts of radio-labeled N-methyl erythromycin to which various amounts of cold erythromycin were added as indicated on the X axis. The rate of production of radio-labeled carbon dioxide was determined and the maximal rate of demethylation of both labeled and unlabeled erythromycin (ERM D max) was then calculated for each rat. Each point represents the value obtained from a single rat. Thusly, the ability to convert radio-labeled carbon to breath carbon dioxide is saturable as shown in FIG. 4, increases dramatically after treatment with dexamethazone as shown in FIG. 4 and correlates well with the erythromycin demethylase activity of the liver microsomes, as illustrated in FIG. 5.

Figure 5:
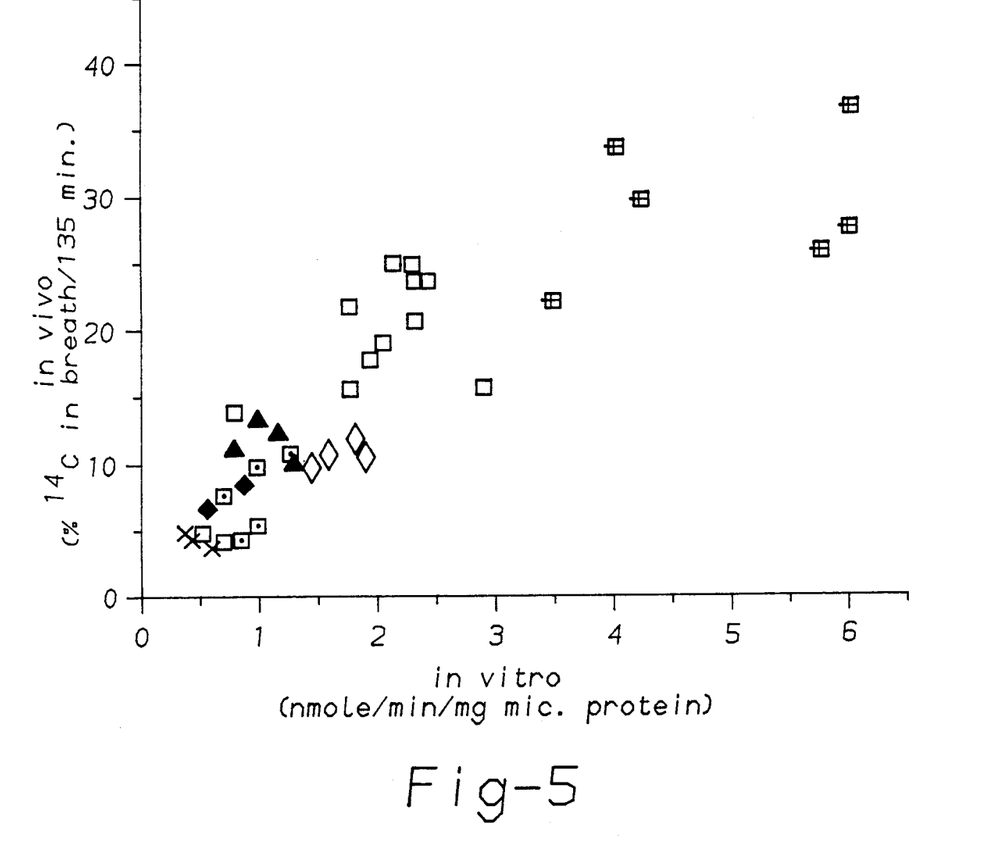
FIG. 5 is a plot showing erythromycin demethylase activity measured in rats (in vivo) and in the corresponding liver microsomes (in vitro) in response to various inducers.
Figure 6:
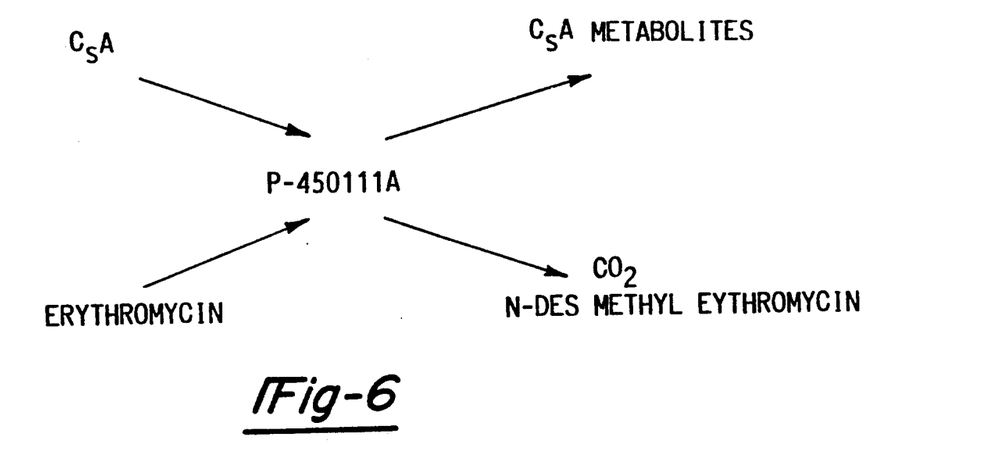
FIG. 6 is a schematic representation of the rationale for the experimental study of cytochrome P-450IIIA catalyzing both the metabolism of CsA and the N-demethylation of erythromycin.
Figure 7A:
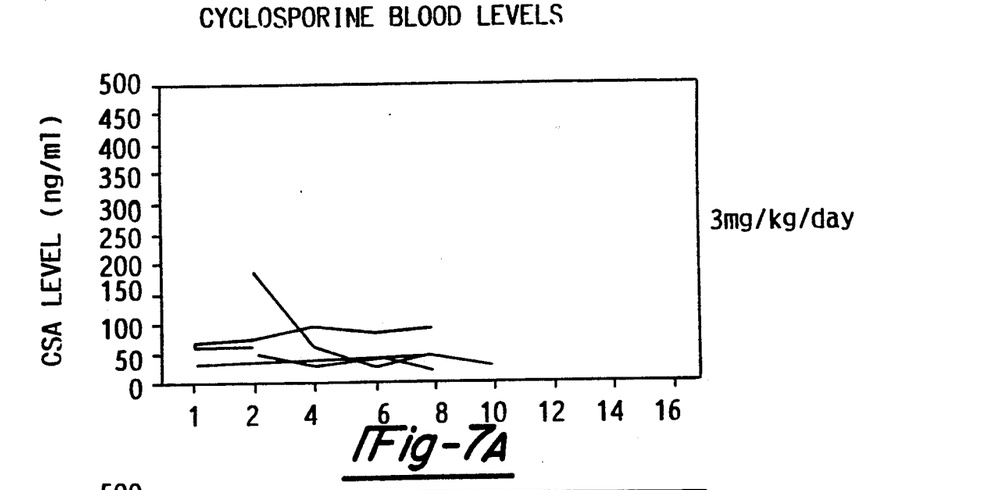
FIG. 7 is a graphic depiction of CsA blood levels observed in patients receiving three different doses, each line connecting the CsA blood level for an individual patient.
Figure 7B:
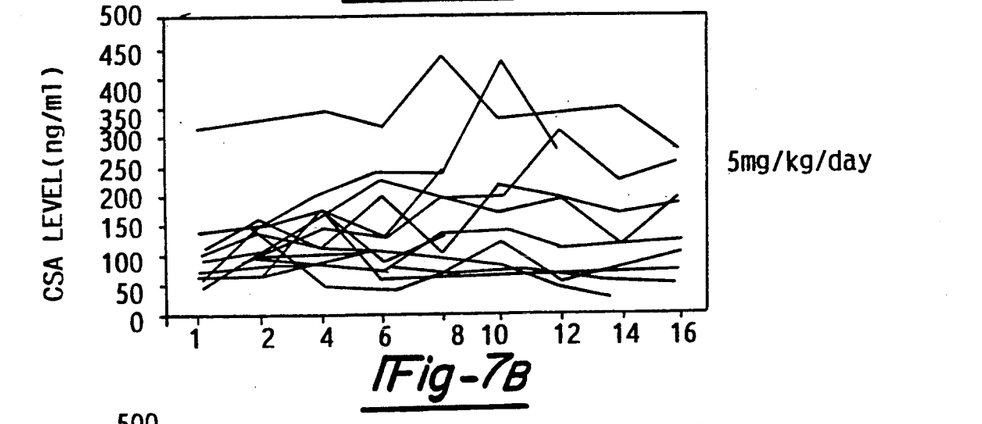
Figure 7C:
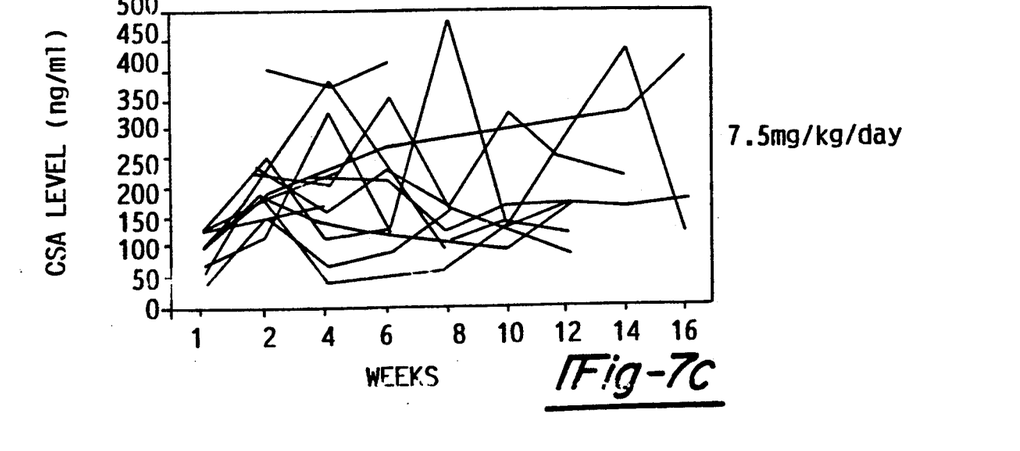
Figure 8:
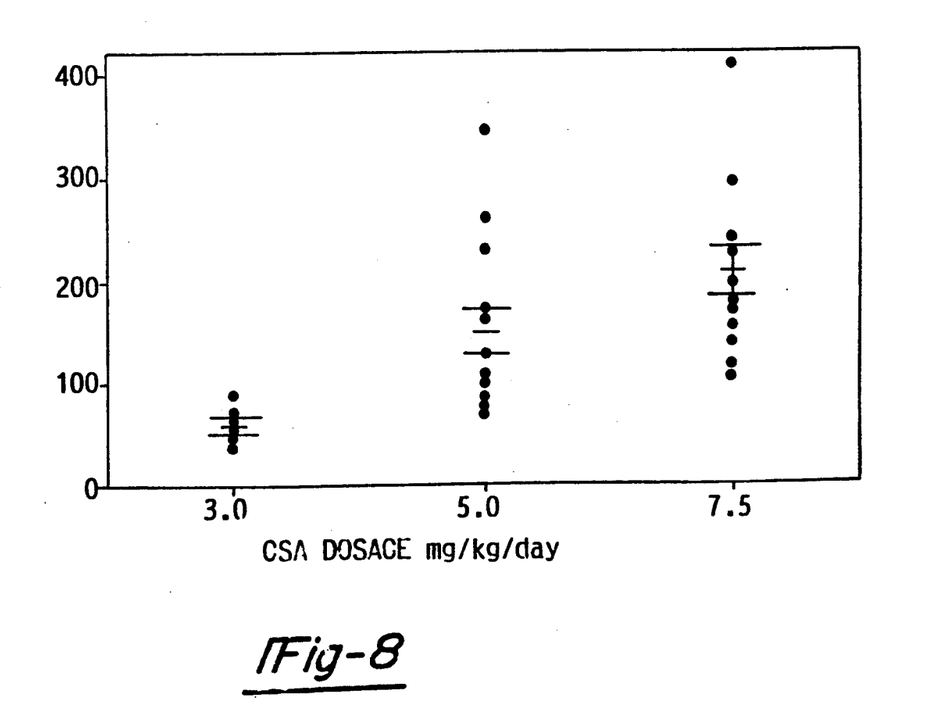
FIG. 8 is a graphic depiction showing mean CsA blood levels observed for each of three doses tested, each point representing one patient's mean CsA level, the small horizontal bars indicating the mean for each group, and wider bars indicating one standard error of the means.
Figure 9:
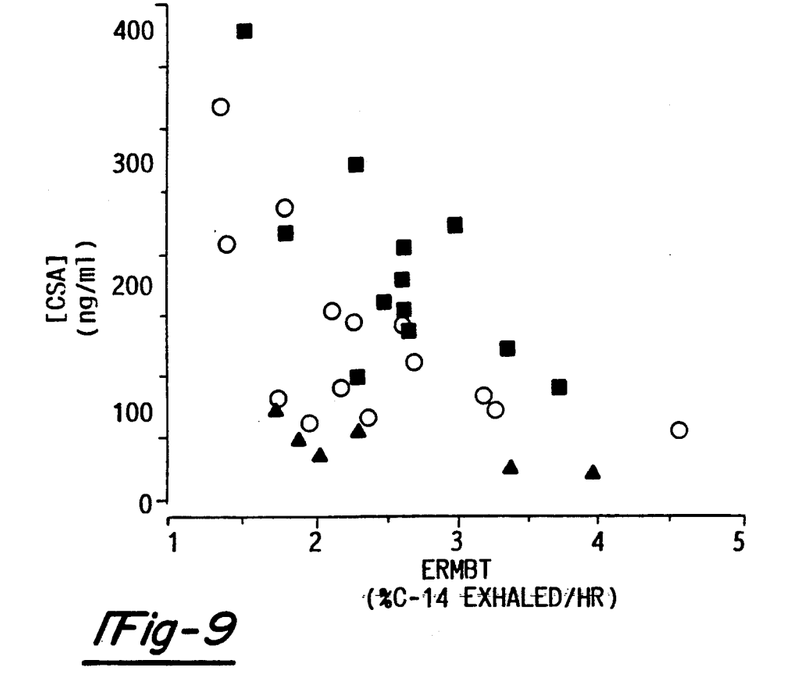
FIG. 9 is a graphic depiction of a correlation between the erythromycin breath test result and mean CsA blood levels, each point representing the mean CsA blood level set forth in FIG. 8 and the erythromycin breath test result (ERMBT) obtained in a single patient, the symbol denoting the dose of CsA each patient received; —3.0 mg/kg/day; O—5.0 mg/kg/day; —7.5 mg/kg/day.
Figure 10:
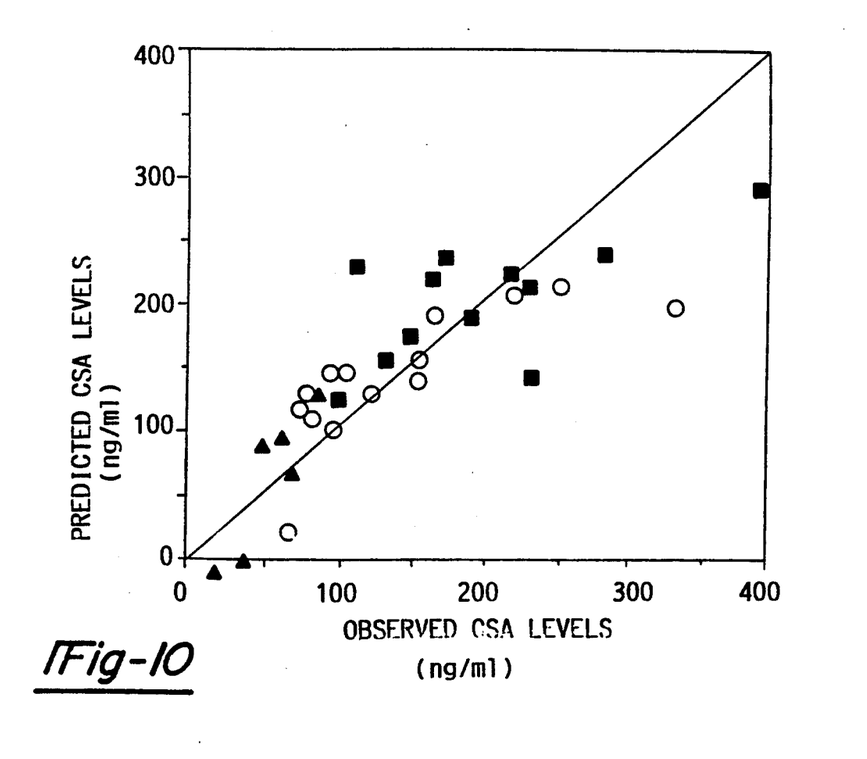
FIG. 10 is a graphic depiction of a comparison of predicted and observed CsA levels; for each patient, the predicted CsA blood level being derived by the mathematical model set forth in Table 3 and compared to the mean CsA blood level actually observed, the symbols denoting the dosage each patient received; -3.0 mg/kg/day; O—5.0 mg/kg/day; —7.5 mg/kg/day.

FIG. 5 illustrates erythromycin demethylase activity measured in rat (in vivo) and corresponding liver microsomes (in vitro) in response to various inducers. Adult female rats were treated with high dose (300 mg/kg/day $\times$3) or low dose (20mg/kg/day) dexamethazone or with compounds that induce cytochromes P-450 other than P-450p. Each rat was then given the erythromycin breath test (in vivo) and immediately sacrificed. The breath test was then compared with the erythromycin demethylase activity determined in the liver microsomes prepared from each rat. Each point on the plot represents the values obtained from a single rat (box containing square being high dose, empty box being low dose, solid triangle being phenobarbital, open diamond being pyrazole, xxx being 3-methyl cholanthrene, closed diamond being clofibrate, and square containing dot being vehicle alone or control.

The results indicate that the erythromycin breath test in accordance with the instant invention is a specific assay for the catalytic activity of P-450p in animals with induced levels of P-450p. However, enzymes other than P-450p may also catalyse erythromycin demethylation. These extensive experiments in rats were carried out because comparison of breath tests results with biochemical analysis of non-diseased liver is not generally possible in patients. However, in patient tests it was found that human liver microsomes prepared from both untreated and glucocorticoid treated patients indicated erythromycin demethylase activity is almost completely blocked by anti-P-450p IgG. Moreover, the total elimination of radio-label in breath during the one hour after injection of the radio-labeled erythromycin increased significantly in each of four patients after treatment with dexamethasone. These results are consistent with prior observations that the concentration of p-450IIIA protein and p-450IIIA mRNA was highest in liver biopsies obtained from patients receiving dexamethazone at the time of surgery and that dexamethazone stimulates production of p-450IIIA mRNA in human hepatoma cell line Hep G2. Mollowa et al, (1986) Proc. Natl. Acad Sci. U.S.A. 83:5311–5315.

The test done in accordance with the present invention should be extremely valuable and important in adequately managing transplant patients on CsA. Applicant therefore administered the subject inventive breath test to 32 patients scheduled to receive CsA to treat psoriasis. The following data found that, for most patients studied, the steady state CsA blood level could be accurately predicted by a simple equation incorporating the subject inventive breath test results, the patients age, and the dose of CsA received. In addition to monitoring CsA, the test may be administered to any patient prior to receiving the medication nifedipine or quinidine as these drugs are known to have low therapeutic index and great interpatient variability in pharmacological effect. It is very likely that this test done in accordance with the present invention will predict the optimal dosing of many other, yet unidentified medications requiring p-450IIIA catalytic activity.

Because a single breath collection in ten minutes appears to be all that is necessary to assess the catalytic activity of p-450IIIA in vivo, the tests should be able to be performed with as little as one microcurie of radio-labeled erythromycin. A commercial kit can contain one or two microcuries of radio-labeled N-methyl erythromycin dissolved in a small quantity of ethanol in a sealed vial and a single scintillation counting vial containing four milliliters of hyamine/ethanol/phenolphthaline solution can be marketed for single breath collection at ten minutes. The kit could also include a syringe and butterfly needle for administration of the radio-label. A vial containing two or three milliliters of dextrose/water solution to mix with the radio-label prior to its administration, and a valved device for blowing bubbles into the container would also be included. This would allow a physician in an in-office or hospital setting to rapidly administer the breath test and then to send the sealed vial to a laboratory for a scintillation counting.

What is claimed is:

1. A method for determining the dosing of a drug metabolized by the P-450 IIIA subfamily of enzymes in a patient, said method consisting essentially of the steps of: ingesting a known quantity of a N-methyl carbon labeled erythromycin, the N-methyl carbon demethylated from the erythromycin being metabolized to an exhaled labeled gaseous carbon dioxide; collecting a sample of exhaled breath containing a known amount of the exhaled carbon dioxide at a known interval of time after ingestion of the labeled erythromycin; detecting the quantity of labeled carbon dioxide in the exhaled sample to determine the rate of labeled carbon elimination after the known time interval as an indication of P-450IIIA subfamily of enzymes function, and predicting dosage of the drug or blood levels of the drug from the indication of the P-450IIIA subfamily of enzymes function.

2. A method as set forth in claim 1 wherein said ingesting step is further defined as orally ingesting a known quantity of the N-methyl carbon labeled erythromycin.

3. A method as set forth in claim 1 further defined as administering to a patient one to three microcuries of $^{14}C$ N-methyl erythromycin dissolved in two milliliters of dextrose and water by intravenous injection; collecting the exhaled breath of the patient ten minutes after administration by patient blowing through a one way valve and tube into a vessel containing four milliliters of 0.5M hyamine in ethanol containing a small amount of phenolphthaline; trapping two millimoles of carbon dioxide in the vessel changing the color of the solution from blue to clear as the trapped carbon dioxide changes the pH of the solution; and detecting the $^{14}C$ activity of the solution by scintillation counting to determine the rate of labeled carbon eliminated after the known time interval.

4. A method as set forth in claim 1 further including the step of predicting dosage of a drug and drug blood levels from the indication of the unique cytochrome P-450 function.

5. A method as set forth in claim 1 wherein the drug is cyclosporine A.

6. A method as set forth in claim 1 wherein said collecting step is further defined as blowing through a one way valve into a vessel containing a known quantity of hyamine and trapping a known quantity of the exhaled carbon dioxide by the reaction of the hyamine with the carbon dioxide.

7. A method as set forth in claim 6 wherein the vessel contains a pH indicator, the blowing step being further defined as blowing bubbles through a one way valved mouth piece into the vessel containing the hyamine dissolved in ethanol, the pH indicator indicating when the known amount of carbon dioxide is trapped.

* * * * *